United States Patent
Zhang et al.

(10) Patent No.: US 12,227,534 B2
(45) Date of Patent: Feb. 18, 2025

(54) METHOD FOR PREPARING NICOTINAMIDE MONONUCLEOTIDE BY USING NICOTINAMIDE AS RAW MATERIAL

(71) Applicant: BONTAC BIO-ENGINEERING(SHENZHEN) CO., LTD., Shenzhen (CN)

(72) Inventors: Guiping Zhang, Shenzhen (CN); Haojie Xu, Shenzhen (CN); Qin Wang, Shenzhen (CN); Zhang Zhang, Shenzhen (CN); Qi Zhang, Shenzhen (CN)

(73) Assignee: BONTAC BIO-ENGINEERING(SHENZHEN) CO., LTD., Guangdong (CN)

( * ) Notice: Subject to any disclaimer, the term of this patent is extended or adjusted under 35 U.S.C. 154(b) by 666 days.

(21) Appl. No.: 17/623,989

(22) PCT Filed: Jun. 19, 2020

(86) PCT No.: PCT/CN2020/096908
§ 371 (c)(1),
(2) Date: Dec. 30, 2021

(87) PCT Pub. No.: WO2021/253362
PCT Pub. Date: Dec. 23, 2021

(65) Prior Publication Data
US 2022/0363704 A1    Nov. 17, 2022

(51) Int. Cl.
*C07H 1/06*  (2006.01)
*C07H 19/048*  (2006.01)

(52) U.S. Cl.
CPC ............. *C07H 1/06* (2013.01); *C07H 19/048* (2013.01)

(58) Field of Classification Search
None
See application file for complete search history.

(56) References Cited

U.S. PATENT DOCUMENTS 10,316,054 B2 *  6/2019  Szczepankiewicz ..... A61P 3/06

OTHER PUBLICATIONS

CN102605026A, machine translation. (Year: 2012).*

* cited by examiner

*Primary Examiner* — Layla D Berry
(74) *Attorney, Agent, or Firm* — Muncy, Geissler, Olds & Lowe, P.C.

(57) ABSTRACT

The invention relates to a method for preparing nicotinamide mononucleotide by using nicotinamide as a raw material, which comprises: in acetonitrile, dichloromethane, 1,2-dichloroethane or liquid sulfur dioxide as a solvent, allowing nicotinamide and tetraacetyl ribose to react as catalyzed by trimethylsilyl trifluoromethanesulfonate or tin tetrachloride, adjusting a pH value thereof to 3-5, adding a sodium methoxide solution thereto to react at −15° C. to 5° C., adjusting a pH value thereof to 3-5, and subjecting the reaction mixture to microfiltration and nanofiltration using a membrane concentrator, thereby obtain a nicotinamide ribose solution; allowing the nicotinamide ribose solution to react as catalyzed by nicotinamide ribokinase in the presence of Mg ions, ATP and a buffer, thereby obtaining nicotinamide mononucleotide. The method of the invention omits the step of refining nicotinamide ribose, and thus has simpler process, lower cost and less time consumption, and has the advantages of faster reaction speed and lower enzyme consumption compared with the enzyme catalytic process directly using refined nicotinamide ribose solid.

10 Claims, No Drawings

METHOD FOR PREPARING NICOTINAMIDE MONONUCLEOTIDE BY USING NICOTINAMIDE AS RAW MATERIAL

TECHNICAL FIELD

The invention relates to the technical field of preparation of nicotinamide mononucleotide, in particular to a method for preparing nicotinamide mononucleotide by using nicotinamide as a raw material through chemical synthesis combined with bio-enzymatic catalysis.

BACKGROUND

Nicotinamide mononucleotide (NMN for short) is an inherent biochemical substance in biological cells, and it can be adenylated by nicotinamide nucleotide adenosine transferase to convert into nicotinamide adenine dinucleotide (NAD for short, also known as coenzyme I) which is an important substance for the survival of biological cells. NMN is a direct precursor of NAD and represents the most ideal way to supplement NAD at present. The level of NMN in biological cells directly affects the concentration of NAD, and NMN plays an important role in the energy generation of biological cells. Also, NMN is not harmful to human body.

Up to now, nicotinamide mononucleotide has been found to have many pharmacological activities. For example, it can regulate immunity and insulin secretion, and affect mRNA expression. It has been developed for medical care such as delaying aging, improving symptoms of senile diseases such as Parkinson's disease. Other uses of NMN are also under investigation. With the increasing awareness of the medicinal and health-care effects of nicotinamide mononucleotide and its wide application as a reaction substrate in the chemical industry, the market demand for nicotinamide mononucleotide is increasing.

Nicotinamide is an amide compound of nicotinic acid and belongs to the precursor of NMN. It is a well-known common method to prepare nicotinamide mononucleotide using nicotinamide as a raw material. This method generally adopts a chemical synthesis route shown below, where firstly nicotinamide is converted into an intermediate product nicotinamide ribose (NR for short), and then the nicotinamide ribose is converted into the end product nicotinamide mononucleotide. Because the method needs to strictly control the water content in the reaction system in the process of converting nicotinamide ribose into nicotinamide mononucleotide, the intermediate product nicotinamide ribose obtained in the previous step must be refined and dehydrated before being fed to participate in the next step of reaction, which leads to the defects of complex process and high production cost.

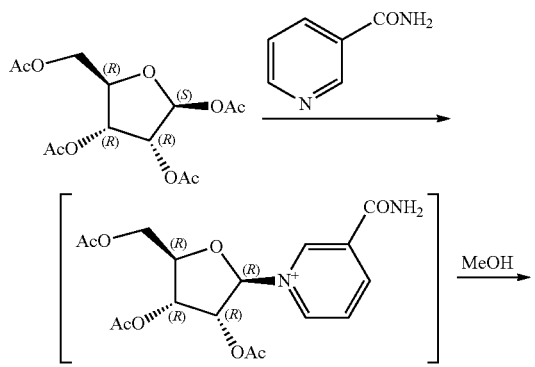

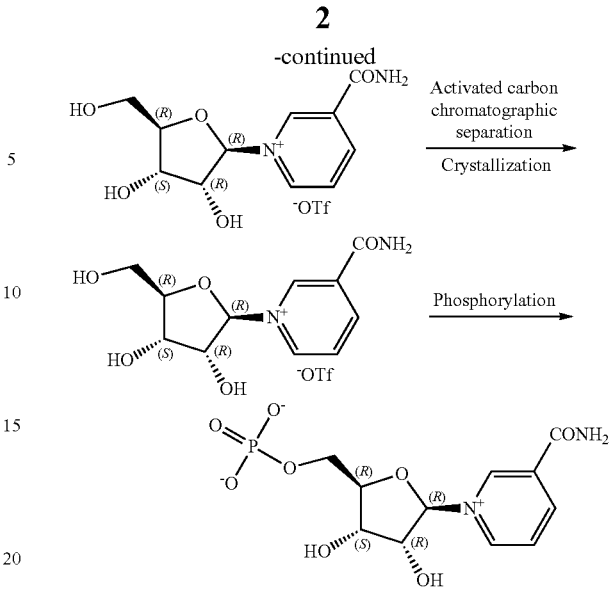

In addition to chemical synthesis, there is currently a method for preparing nicotinamide mononucleotide using nicotinamide ribose as a raw material by bio-enzymatic catalysis. The whole reaction system of this method is aqueous, and therefore moisture control is not required. However, in order to ensure that the biological enzyme used in the catalytic process is stable and can be recycled, refined nicotinamide ribose is often used as a raw material, which leads to high production cost.

SUMMARY

In view of the above defects mentioned in the background of the invention, an objective of the invention is to solve the technical problem that the reaction for converting into nicotinamide mononucleotide can be completed only by using refined nicotinamide ribose, and to develop a method for preparing nicotinamide mononucleotide by using nicotinamide as a raw material with simple process and low cost through chemical synthesis combined with green and environment-friendly bio-enzymatic catalysis.

In order to achieve the above objective, the inventor has carried out numerous experiments over a long time and finally developed a method for preparing nicotinamide mononucleotide by using nicotinamide as a raw material, which comprises the following steps:

1) allowing nicotinamide and tetraacetyl ribose to react in acetonitrile, dichloromethane, 1,2-dichloroethane or liquid sulfur dioxide as a solvent as catalyzed by trimethylsilyl trifluoromethanesulfonate or tin tetrachloride at a temperature of 20-40° C. to obtain a first reaction mixture;
2) adding sodium bicarbonate, sodium carbonate or sodium hydroxide into the first reaction mixture to adjust a pH value thereof to 3-5 to obtain a second reaction mixture;
3) adding a sodium methoxide solution into the second reaction mixture to react at a temperature of −15° C. to 5° C. to obtain a third reaction mixture;
4) adding hydrochloric acid into the third reaction mixture to adjust a pH value thereof to 3-5 to obtain a fourth reaction mixture;
5) performing microfiltration and nanofiltration on the fourth reaction mixture in sequence by using a membrane concentrator to obtain a nicotinamide ribose solution; and 6) allowing the nicotinamide ribose solution obtained in the step 5) to react as catalyzed by nicotinamide ribokinase at a temperature of 35-39° C. in the presence of Mg ions, ATP and a buffer, wherein a pH value of the reaction mixture is controlled at 7.5-8.0 during the reaction, and nicotinamide mononucleotide is obtained after the reaction is complete.

In consideration of energy consumption and reaction speed together, in the method for preparing nicotinamide mononucleotide by using nicotinamide as a raw material provided by the invention, the reaction in the step 1) is preferably carried out at a temperature of 25-35° C.

In the step 1) of the method for preparing nicotinamide mononucleotide by using nicotinamide as a raw material provided by the invention, the solvent is preferably acetonitrile, which provides good solubility in the reaction, facilitates forming a homogeneous system, contributing to rapid reaction and very little by-product alpha-isomer (<0.1%).

In the step 1) of the method for preparing nicotinamide mononucleotide by using nicotinamide as a raw material provided by the invention, the catalyst is preferably trimethylsilyl trifluoromethanesulfonate, which has high reaction stereoselectivity in the reaction, is easy to process and results in no metal residue.

Preferably, in the step 1) of the method for preparing nicotinamide mononucleotide by using nicotinamide as a raw material provided by the invention, the molar ratio of trimethylsilyl trifluoromethanesulfonate or tin tetrachloride to nicotinamide to tetraacetyl ribose is 1.2-5:1.2-2:1.

Preferably, in the method for preparing nicotinamide mononucleotide using nicotinamide as a raw material provided by the invention, before the step 3), the second reaction mixture is concentrated first to remove the solvent.

In consideration of energy consumption and product stability together, preferably, in the method for preparing nicotinamide mononucleotide by using nicotinamide as a raw material provided by the invention, the reaction in the step 3) is carried out at the temperature of −10° C. to −5° C.

Preferably, in the step 3) of the method for preparing nicotinamide mononucleotide by using nicotinamide as a raw material provided by the invention, the molar ratio of sodium methoxide to tetraacetyl ribose is 1-5:1.

In consideration of energy consumption and product stability, preferably, in the method for preparing nicotinamide mononucleotide by using nicotinamide as a raw material provided by the invention, the temperature of the reaction mixture is maintained at −10° C. to −5° C. in the step 4).

Preferably, in the step 5) of the method for preparing nicotinamide mononucleotide by using nicotinamide as a raw material provided by the invention, a microfiltration membrane with a pore size of 0.2-1 μm is used in the microfiltration process so as to remove microorganisms and large particle molecules in the reaction mixture, and a hollow fiber membrane with a molecular weight cutoff of 150-250 is used in the nanofiltration process so as to remove nicotinamide, residual solvent and most of inorganic salt impurities in the reaction mixture.

Preferably, in the step 6) of the method for preparing nicotinamide mononucleotide by using nicotinamide as a raw material provided by the invention, the Mg ion, the ATP, the buffer, the nicotinamide ribose and the nicotinamide ribokinase are added at an amount of 10-50 mM, 10-30 mM, 20-100 mM, 9-27 mM and 0.2-1 g/L respectively.

Preferably, in the step 6) of the method for preparing nicotinamide mononucleotide by using nicotinamide as a raw material provided by the invention, the Mg ion is $MgCl_2$.

Preferably, in the step 6) of the method for preparing nicotinamide mononucleotide by using nicotinamide as a raw material provided by the invention, the buffer is $K_2HPO_4$ buffer.

BENEFICIAL EFFECTS

Compared with the prior art, the method for preparing nicotinamide mononucleotide provided by the invention uses nicotinamide and tetraacetyl ribose as initial raw materials and nicotinamide ribose as a reaction intermediate, and the whole process avoids the technical requirement in the prior art that nicotinamide ribose needs to be refined by methods such as crystallization before participating in the subsequent reaction for converting into nicotinamide mononucleotide, so that the step of refining nicotinamide ribose is omitted; and the process is simpler, the operation is simpler, the cost is lower, and the time consumption is less. Meanwhile, when the unrefined nicotinamide ribose solution synthesized by the method of the invention is applied to the subsequent enzyme-catalyzed reaction for preparing nicotinamide mononucleotide, unexpected advantages such as higher reaction speed, lower enzyme consumption are obtained compared with when refined nicotinamide ribose solid is used directly. Also, the process time is further shortened and the cost is reduced. In addition, bio-enzymatic catalysis is introduced on the basis of chemical synthesis, which makes the method of the invention is more green and environment-friendly compared with chemical synthesis alone.

BRIEF DESCRIPTION OF THE DRAWINGS

Detailed Description of the Embodiments

The invention is further described in detail below with reference to specific examples, which are illustrative of the invention, and the invention is not limited to the following examples.

The raw materials and reagents used in the following examples, unless otherwise specified, were purchased from the market.

Example 1

Preparation of Intermediate Product Nicotinamide Ribose Solution

Under nitrogen protection, 100 g of tetraacetyl ribose (314.5 mmol, 1.0 eq), 115.1 g of nicotinamide (943.4 mmol, 3 eq) and 700 ml of acetonitrile were sequentially added into a 2 L three-necked flask, and stirred at 20° C. to obtain a suspension. 170.3 ml (943.4 mmol, 3 eq) of trimethylsilyl trifluoromethanesulfonate was slowly added dropwise, during which the suspension became clear and then turned cloudy. The stirring was continued for 45 min at 20° C., and at that time, sample dispensing on the plate showed that the raw materials were completely converted. Sodium bicarbonate was added into the reaction mixture to adjust the pH value to 3-5, and the mixture was concentrated by distillation to remove the solvent, thereby obtaining a pale yellow oily liquid (yield 100%).

The obtained pale yellow oily liquid was dissolved in 500 ml of methanol, cooled to −10° C. with stirring, and 314.5 ml (1572.5 mmol, 5 eq) of a sodium methoxide solution was slowly added dropwise thereto while keeping the internal temperature of the reaction mixture below −5° C. Thereafter, the reaction was carried out at −5° C. to −10° C. for 40 min, and at that time, high performance liquid chromatography (HPLC) showed that the raw materials were completely converted. To the reaction mixture, 250 mL (1500 mmol) of 6 M hydrochloric acid was slowly added dropwise to adjust the pH value to 3-4, and the reaction mixture was concentrated to obtain a pale yellow liquid (yield 100%).

The obtained pale yellow liquid was dissolved in water, and then fed into a membrane concentrator to receive microfiltration and nanofiltration in sequence, wherein a microfiltration membrane with a pore size of 0.2 μm was used in the microfiltration process, and a hollow fiber membrane with a molecular weight cutoff of 150 was used in the nanofiltration process, thereby obtaining a nicotinamide ribose solution (with residual organic solvent of less than 0.5%) for later use.

Example 2

Preparation of Intermediate Product Nicotinamide Ribose Solution

Under nitrogen protection, 100 g of tetraacetyl ribose (314.5 mmol, 1.0 eq), 76.7 g of nicotinamide (628.7 mmol, 2 eq) and 700 ml of dichloromethane were sequentially added into a 2 L three-necked flask, and stirred at 25° C. to obtain a suspension. 113.5 ml (628.7 mmol, 2 eq) of trimethylsilyl trifluoromethanesulfonate was slowly added dropwise thereto, followed by stirring at 25° C. for 50 min, whereupon the raw materials were completely converted. Sodium bicarbonate was added into the reaction mixture to adjust the pH value to 3-5, and the mixture was concentrated by distillation to remove the solvent, thereby obtaining a pale yellow oily liquid (yield 100%).

The obtained pale yellow oily liquid was dissolved in 500 ml of methanol, cooled to −10° C. with stirring, and 188.7 ml (943.5 mmol, 3 eq) of a sodium methoxide solution was slowly added dropwise thereto while keeping the internal temperature of the reaction mixture below −5° C. Thereafter, the reaction was carried out at −5° C. to −10° C. for 60 min, whereupon the raw materials were completely converted. To the reaction mixture, 150 mL (900 mmol) of 6 M hydrochloric acid was slowly added dropwise to adjust the pH value to 3-4, and the reaction mixture was concentrated to obtain a pale yellow liquid (100% yield).

The obtained pale yellow liquid was dissolved in water, and then fed into a membrane concentrator to receive microfiltration and nanofiltration in sequence, wherein a microfiltration membrane with a pore size of 0.5 μm was used in the microfiltration process, and a hollow fiber membrane with a molecular weight cutoff of 200 was used in the nanofiltration process, thereby obtaining a nicotinamide ribose solution (with residual organic solvent of less than 0.5%) for later use.

Example 3

Preparation of Intermediate Product Nicotinamide Ribose Solution

Under nitrogen protection, 100 g of tetraacetyl ribose (314.5 mmol, 1.0 eq), 57.5 g of nicotinamide (471.3 mmol, 1.5 eq) and 700 ml of 1,2-dichloroethane were added into a 2 L three-necked flask, and stirred at 35° C. to obtain a suspension. 85.1 ml (471.3 mmol, 1.5 eq) of tin tetrachloride was slowly added dropwise thereto, followed by stirring at 35° C. for 45 min, whereupon the raw materials were completely converted. Sodium carbonate was added into the reaction mixture to adjust the pH value to 3-5, and the mixture was concentrated by distillation to remove the solvent, thereby obtaining a pale yellow oily liquid (yield: 100%).

The obtained pale yellow oily liquid was dissolved in 500 ml of methanol, cooled to −10° C. with stirring, and 125.8 ml (629 mmol, 2 eq) of a sodium methoxide solution was slowly dropwise added thereto while keeping the internal temperature of the reaction mixture below −5° C. Thereafter, the reaction was carried out at −5° C. to −10° C. for 90 min, whereupon the raw materials were completely converted. To the reaction mixture, 100 mL (600 mmol) of 6 M hydrochloric acid was slowly added dropwise to adjust the pH value to 3-5, and the reaction mixture was concentrated to obtain a pale yellow liquid (100% yield).

The obtained pale yellow liquid was dissolved in water, and then fed into a membrane concentrator to receive microfiltration and nanofiltration in sequence, wherein a microfiltration membrane with a pore size of 0.7 μm was used in the microfiltration process, and a hollow fiber membrane with a molecular weight cutoff of 200 was used in the nanofiltration process, thereby obtaining a nicotinamide ribose solution (with residual organic solvent of less than 0.5%) for later use.

Example 4

Preparation of Intermediate Product Nicotinamide Ribose Solution

Under nitrogen protection, 100 g of tetraacetyl ribose (314.5 mmol, 1.0 eq), 46 g of nicotinamide (377 mmol, 1.2 eq) and 700 ml of liquid sulfur dioxide were added into a 2 L three-necked flask, and stirred at 40° C. to obtain a suspension. 68.0 ml (377 mmol, 1.2 eq) of trimethylsilyl trifluoromethanesulfonate was slowly added dropwise thereto, followed by stirring at 40° C. for 45 min, whereupon the raw materials were completely converted. Sodium hydroxide was added into the reaction mixture to adjust the pH value to 3-5, and the mixture was concentrated by distillation to remove the solvent, thereby obtaining a pale yellow oily liquid (yield: 100%).

The obtained pale yellow oily liquid was dissolved in 500 ml of methanol, cooled to −10° C. with stirring, and 94.3 ml (471.7 mmol, 1.5 eq) of a sodium methoxide solution was slowly dropwise added thereto while keeping the internal temperature of the reaction mixture below −5° C. Thereafter, the reaction was carried out at −5° C. to −10° C. for 120 min, whereupon the raw materials were completely converted. To the reaction mixture, 75 mL (450 mmol) of 6 M hydrochloric acid was slowly added dropwise to adjust the pH value to 3-5, and the reaction mixture was concentrated to obtain a pale yellow liquid (100% yield).

The obtained pale yellow liquid was dissolved in water, and then fed into a membrane concentrator to receive microfiltration and nanofiltration in sequence, wherein a microfiltration membrane with a pore size of 1 μm was used in the microfiltration process, and a hollow fiber membrane with a molecular weight cutoff of 250 was used in the nanofiltration process, thereby obtaining a nicotinamide ribose solution (with residual organic solvent of less than 0.5%) for later use.

Example 5

The results of various parameters in the preparation of the intermediate product nicotinamide ribose solution are shown in Table 1 to Table 5.

TABLE 1

Effects of nicotinamide/trimethylsilyl trifluoromethanesulfonate dosage on reaction conversion

| Experiment | Nicotinamide dosage | Trimethylsilyl trifluoromethane-sulfonate/tin tetrachloride dosage | Reaction conversion |
|---|---|---|---|
| 1 | 1.0 eq | 1.0 eq | Excessive tetraacetyl ribose |
| 2 | 1.2 eq | 1.2 eq | Complete reaction |
| 3 | 1.5 eq | 2.0 eq | Complete reaction |
| 4 | 2.0 eq | 5.0 eq | Complete reaction |

TABLE 2

Effects of pH adjustment with sodium bicarbonate on the long-term stability of nicotinamide ribose solution

| Experiment | pH | Temperature | Storage time | Stability |
|---|---|---|---|---|
| 1 | 3 | 2-4° C. | 45 days | Substantially no degradation |
| 2 | 4 | 2-4° C. | 45 days | 2.4% degradation |
| 3 | 5 | 2-4° C. | 45 days | 3.7% degradation |

TABLE 3

Effects of temperature on reaction in step 3)

| Temperature | Sodium methoxide dosage | Reaction time | Reaction result |
|---|---|---|---|
| 0-5° C. | 2.0 eq | 0.5 h | Complete reaction and 9.2% product degradation |
| −5° C. to 0° C. | 2.0 eq | 1.0 h | Complete reaction and 19.6% product degradation |
| −10° C. to −5° C. | 2.0 eq | 1.5 h | Complete reaction and substantially no product degradation |
| −15° C. to −10° C. | 2.0 eq | 5.0 h | Complete reaction and substantially no product degradation |

TABLE 4

Effects of sodium methoxide dosage on reaction in step 3)

| Sodium methoxide dosage | Reaction temperature | Reaction time | Reaction result |
|---|---|---|---|
| 1.2 eq | −10° C. to −5° C. | 24.0 h | Complete reaction and substantially no product degradation |
| 1.5 eq | −10° C. to −5° C. | 2.0 h | Complete reaction and substantially no product degradation |
| 2.0 eq | −10° C. to −5° C. | 1.5 h | Complete reaction and substantially no product degradation |
| 3.0 eq | −10° C. to −5° C. | 1.0 h | Complete reaction and substantially no product degradation |
| 5.0 eq | −10° C. to −5° C. | 40 min | Complete reaction and substantially no product degradation |

TABLE 5

Effects of pH adjustment with hydrochloric acid on the long-term stability of nicotinamide ribose solution

| Experiment | Storage temperature | pH | Storage time | Stability |
|---|---|---|---|---|
| 1 | 0-4° C. | 3 | 45 days | Substantially no degradation |
| 2 | 0-4° C. | 4 | 45 days | 1.3% degradation |
| 3 | 0-4° C. | 5 | 45 days | 2.1% degradation |

Example 6

Preparation of Nicotinamide Mononucleotide

TABLE 6

| Material | Concentration | Amount per 100 mL |
|---|---|---|
| K2HPO4 | 50 mM | 2.28 g |
| MgCl2 | 10 mM | 0.41 g |
| ATP | 20 mM | 1.10 g |
| Commercially available NR solid (content 80%)/NR solution prepared in example of the invention (content 300 mM) | 18 mM | 0.65 g/6 ml |
| Nicotinamide ribokinase | 0.33-0.5 g/L | |

1 g of nicotinamide ribokinase was weighed and prepared into an enzyme working solution with 10 mL of pure water, and stored at 4° C.

The first three materials were each weighed according to Table 6 and dissolved with about 70 mL of pure water respectively, and then the commercial NR solid (content 80%) or the NR solution prepared according to the example of the invention (content 300 mM) was added thereto respectively. The mixture was adjusted to a pH value of 7.5-8.0 with 3 M NaOH, and made up to a volume of 100 mL. After preheating the mixture at 37° C., 330-500 μL of the enzyme working solution was added and the mixture was subjected to a constant-temperature oscillation reaction at 220 rpm. After the reaction was completed, nicotinamide mononucleotide was obtained.

Samples were taken every half hour during the reaction, and the product formation was analyzed by HPLC, with pH monitored and regulated, and the results are shown in Table 7:

TABLE 7

| Substrate type | Enzyme amount | NR→NMN conversion | | |
|---|---|---|---|---|
| | | 0.5 h | 1 h | 1.5 h |
| Commercially available NR solid | 0.5 g/L | 66.4% | 91.6% | 98.5% |
| NR solution prepared by example of the invention | 0.33 g/L | 61.4% | 92.7% | 99.3% |
| NR solution prepared by example of the invention | 0.5 g/L | 79.4% | 96.5% | 99.2% |

As can be seen from table 7, that NR solution prepared in the example of the invention has a faster initial reaction speed and requires a lower amount of enzyme than the commercially available NR solid.

Example 7

Preparation of Nicotinamide Mononucleotide

TABLE 8

| Material | Concentration | Amount per 100 mL |
|---|---|---|
| K2HPO4 | 100 mM | 4.56 g |
| MgCl2 | 20 mM | 0.82 g |
| ATP | 20 mM | 1.10 g |
| Commercially available NR solid (content 50%)/NR solution prepared in example of the invention (content 570 mM) | 18 mM | 1.05 g/3.15 ml |
| Nicotinamide ribokinase | 0.65 g/L | |

1 g of nicotinamide ribokinase was weighed and prepared into an enzyme working solution with 10 mL of pure water, and stored at 4° C.

The first three materials were each weighed according to Table 8 and dissolved with about 70 mL of pure water respectively, and then the commercial NR solid (content 50%) or the NR solution prepared according to the example of the invention (content 570 mM) was added thereto respectively. The mixture was adjusted to a pH value of 7.5-8.0 with 3 M NaOH, and made up to a volume of 100 mL. After preheating the mixture at 37° C., 650 μL of the enzyme working solution was added and the mixture was subjected to a constant-temperature oscillation reaction at 220 rpm. After the reaction was completed, nicotinamide mononucleotide was obtained.

Samples were taken every half hour during the reaction, and the product formation was analyzed by HPLC, with pH monitored and regulated, and the results are shown in Table 9:

TABLE 9

| Substrate type | Enzyme amount | NR→NMN conversion | | |
|---|---|---|---|---|
| | | 0.5 h | 1 h | 1.5 h |
| Commercially available NR solid - lot 1 | 0.65 g/L | 76.3% | 85.0% | 94.1% |
| Commercially available NR solid - lot 2 | 0.65 g/L | 29.7% | 34.9% | 36.7% |
| NR solution prepared in example of the invention - lot 1 | 0.65 g/L | 87.2% | 97.0% | 99.6% |
| NR solution prepared in example of the invention - lot 2 | 0.65 g/L | 89.6% | 98.1% | 99.8% |

As can be seen from table 9, as compared with the commercial NR solid, the NR solution prepared in the example of the invention has a faster initial reaction speed, and can avoid the phenomenon of reaction inhibition due to the presence of certain impurities that occurred in the commercial NR solid—lot 2.

Example 8

Preparation of Nicotinamide Mononucleotide

TABLE 10

| Material | Concentration | Amount per 100 mL |
|---|---|---|
| K$_2$HPO$_4$ | 20 mM | 0.91 g |
| MgCl$_2$ | 50 mM | 2.05 g |
| ATP | 30 mM | 1.65 g |
| Commercially available NR solid (content 98%)/NR solution prepared in example of the invention (content 1020 mM) | 27 mM | 0.82 g/2.65 ml |
| Nicotinamide ribokinase | 1 g/L | |

1 g of nicotinamide ribokinase was weighed and prepared into an enzyme working solution with 10 mL of pure water, and stored at 4° C.

The first three materials were each weighed according to Table 10 and dissolved with about 70 mL of pure water respectively, and then the commercial NR solid (content 98%) or the NR solution prepared according to the example of the invention (content 1020 mM) was added thereto respectively. The mixture was adjusted to a pH value of 7.5-8.0 with 3 M NaOH, and made up to a volume of 100 mL. After preheating the mixture at 37° C., 1 mL of the enzyme working solution was added and the mixture was subjected to a constant-temperature oscillation reaction at 220 rpm. After the reaction was completed, nicotinamide mononucleotide was obtained.

Samples were taken every half hour during the reaction, and the product formation was analyzed by HPLC, with pH monitored and regulated, and the results are shown in Table 11:

TABLE 11

| Substrate type | Enzyme amount | NR→NMN conversion | | |
|---|---|---|---|---|
| | | 0.5 h | 1 h | 1.5 h |
| Commercially available NR solid | 1 g/L | 77.1% | 83.8% | 86.2% |
| NR solution prepared in example of the invention | 1 g/L | 82.3% | 83.7% | 86.5% |

As can be seen from table 11, as compared with the commercial NR solid, the NR solution prepared in the example of the invention has a slightly faster initial reaction speed, and the conversion will reduce when the substrate concentration is increased.

The invention claimed is:

1. A method for preparing nicotinamide mononucleotide by using nicotinamide as a raw material, wherein the method comprises steps of:
   1) allowing nicotinamide and tetraacetyl ribose to react in acetonitrile, dichloromethane, 1,2-dichloroethane or liquid sulfur dioxide as a solvent as catalyzed by trimethylsilyl trifluoromethanesulfonate or tin tetrachloride at a temperature of 20-40° C. to obtain a first reaction mixture;
   2) adding sodium bicarbonate, sodium carbonate or sodium hydroxide into the first reaction mixture to adjust a pH value thereof to 3-5 to obtain a second reaction mixture;
   3) adding a sodium methoxide solution into the second reaction mixture to react at a temperature of −15° C. to 5° C. to obtain a third reaction mixture;
   4) adding hydrochloric acid into the third reaction mixture to adjust a pH value thereof to 3-5 to obtain a fourth reaction mixture;
   5) performing microfiltration and nanofiltration on the fourth reaction mixture in sequence by using a membrane concentrator to obtain a nicotinamide ribose solution; and
   6) allowing the nicotinamide ribose solution obtained in the step 5) to react as catalyzed by nicotinamide ribokinase at a temperature of 35-39° C. in the presence of Mg ions, ATP and a buffer, wherein a pH value of the reaction mixture is controlled at 7.5-8.0 during the reaction, and nicotinamide mononucleotide is obtained after the reaction is complete.

2. The method for preparing nicotinamide mononucleotide by using nicotinamide as a raw material according to claim 1, wherein the reaction in the step 1) is carried out at a temperature of 25-35° C.

3. The method for preparing nicotinamide mononucleotide by using nicotinamide as a raw material according to claim 1, wherein in the step 1), a molar ratio of the trimethylsilyl trifluoromethanesulfonate to the nicotinamide to the tetraacetyl ribose is 1.2-5:1.2-2:1.

4. The method for preparing nicotinamide mononucleotide by using nicotinamide as a raw material according to claim 1, wherein the reaction in the step 3) is carried out at a temperature of −10° C. to −5° C.

5. The method for preparing nicotinamide mononucleotide by using nicotinamide as a raw material according to claim 1, wherein in the step 3), a molar ratio of the sodium methoxide to the tetraacetyl ribose is 1-5:1.

6. The method for preparing nicotinamide mononucleotide by using nicotinamide as a raw material according to claim 1, wherein during the step 4), the temperature of the reaction mixture is maintained at −10° C. to −5° C.

7. The method for preparing nicotinamide mononucleotide by using nicotinamide as a raw material according to claim 1, wherein in the step 5), a microfiltration membrane with a pore size of 0.2-1 μm is used in the microfiltration process, and a hollow fiber membrane with a molecular weight cutoff of 150-250 is used in the nanofiltration process.

8. The method for preparing nicotinamide mononucleotide by using nicotinamide as a raw material according to claim 1, wherein in the step 6), the Mg ion, the ATP, the buffer, the nicotinamide ribose and the nicotinamide ribokinase are added at an amount of 10-50 mM, 10-30 mM, 20-100 mM, 9-27 mM and 0.2-1 g/L respectively.

9. The method for preparing nicotinamide mononucleotide by using nicotinamide as a raw material according to claim 1, wherein in the step 6), the Mg ion is $MgCl_2$.

10. The method for preparing nicotinamide mononucleotide by using nicotinamide as a raw material according to claim 1, wherein in the step 6), the buffer is $K_2HPO_4$ buffer.

* * * * *